US00PP26822P3

(12) United States Plant Patent
Stefanini

(10) Patent No.: US PP26,822 P3
(45) Date of Patent: Jun. 14, 2016

(54) GRAPEVINE "IASMA ECO 2"

(50) Latin Name: ***Vitis vinifera* L.**
Varietal Denomination: IASMA ECO 2

(71) Applicant: FONDAZIONE EDMUND MACH-CENTRO RICERCA ED INNOVAZIONE, San Michele All'Adige (TN) (IT)

(72) Inventor: Marco Stefanini, Bolzano (IT)

(73) Assignee: FONDAZIONE EDMUND MACH-CENTRO RICERCA ED INNOVAZIONE, San Michele All'Adige (IT)

( * ) Notice: Subject to any disclaimer, the term of this patent is extended or adjusted under 35 U.S.C. 154(b) by 7 days.

(21) Appl. No.: 13/999,223

(22) Filed: Jan. 31, 2014

(65) Prior Publication Data

US 2015/0223382 P1 Aug. 6, 2015

(51) Int. Cl.
*A01H 5/00* (2006.01)

(52) U.S. Cl.
USPC ..... Plt./205

(58) Field of Classification Search
USPC ..... Plt./205
See application file for complete search history.

(56) References Cited

PUBLICATIONS

PLUTO Plant Variety Database Jun. 20, 2015. p. 1.*
U.S. Appl. No. 13/999,222, filed Jan. 31, 2014, Stefani.

* cited by examiner

*Primary Examiner* — Annette Para
(74) *Attorney, Agent, or Firm* — Oblon, McClelland, Maier & Neustadt, L.L.P.

(57) ABSTRACT

This invention is a new and distinct grapevine variety named "IASMA ECO 2" which is characterized by producing red berries which are rounder, less sensitive to *Botrytis cinerea* and with a higher tannin content with respect to the two parents.

3 Drawing Sheets

Latin name of the genus and species claimed: *Vitis vinifera* L.

Variety denomination: "IASMA ECO 2".

CROSS REFERENCE TO RELATED APPLICATIONS

The present application is related to Community Plant Variety application 2012/2343, filed in the Community Plant Variety Office on Oct. 25, 2012, the entire contents of which are hereby incorporated by reference.

BACKGROUND OF THE INVENTION

Discussion of the Background

The new and distinct grapevine described and claimed herein originated from a hand pollinated cross of the Teroldego variety (seed parent) and the Lagrein variety (pollen parent), neither of which are protected by plant patent, plant variety protection certificate, or similar. The seeds were subsequently germinated and the resulting plants were planted in the field. The present variety of grapevine was selected as a single plant, and asexually propagated by hardwood cuttings. The resulting propagules were planted and were found to reproduce true-to-type through at least three generations of asexual reproduction, with the observations taking place from 2004 to 2010 in San Michele All'Adige (TN)—Trentino Alto Adige—Italy (46° 11' Lat. N, 11° 28' Long. E, 235 s.l.m.).

SUMMARY OF THE INVENTION

To the inventor's knowledge, there are no varieties similar to the new variety; being a crossing result, they contain 50% of the genetic material of the seed parent and 50% of the genetic material of the pollen parent.

The present variety produces red berries which are rounder, less sensitive to *Botrytis cinerea* and with a higher tannin content with respect to the two parents.

The variety IASMA ECO 2 differs from the parents Teroldego and Lagrein in having no anthocyanin coloration of the apex, and in the absence of crawling and erect hairs compared to the parents which have a high density of crawling and sparse erect hair.

The young sprout of IASMA ECO 2 has no creeping or erect hairs while its parents have them in a low amount.

The tendrils of the variety IASMA ECO 2 are short, while those of its parents are long.

The young leaves of Teroldego and Lagrein have green NN155C color, and a high density of creeping hairs between the ribs, while the color of the IASMA ECO 2 leaf is green 136D. The hair density between the ribs is medium in IASMA ECO 2.

The mature leaf is large in Lagrein and Teroldego, and has three lobes, while in IASMA ECO 2 it is medium-sized with five lobes. The teeth of IASMA ECO 2 are tiny. One of their sides is concave, one side is rectilinear, as in Lagrein, but it differs from the Teroldego which has convex teeth. The teeth of the parents are medium sized.

The petiole sinus is Brace shaped in the IASMA ECO 2 variety, while in Teroldego it is open V-shaped and open U-shaped in Lagrein. The base of the lateral sinus is V shaped in the parents while in IASMA ECO 2 it is U-shaped and has one tooth. The density of prostrate hairs and of erect hairs between the ribs is high in the parents, and medium and low in the variety IASMA ECO 2.

The section of woody shoot is circular in Teroldego and Lagrein and in IASMA ECO 2 it is elliptic.

The first inflorescence of variety IASMA ECO 2 is on the second node. Its basal bud (1-3) fertility is very high, while insertion of the first inflorescence in Lagrein is at the 3rd and 4th nodes, with medium fertility of the buds; in Teroldego the first inflorescence is at the 5th internode with very low bud fertility. The number of inflorescences per shoot is 1.1 to 2 in the parents and 2.1 to 3 for the variety IASMA ECO 2.

The first inflorescence of IASMA ECO 2 is about 15 cm long and the date of full bloom is generally around June 10, while Lagrein has 15 cm inflorescence, and a date of full bloom in 7th June. The first inflorescence of Teroldego is 20 cm long and the date of full bloom is 7th June.

The cluster of IASMA ECO 2 is very long (>24 cm), medium width (<12 cm) and loose, while Teroldego shows a cluster of similar size but very compact, while in Lagrein the bunches are compact and their length is between 16 and 24 cm and <12 cm broad.

The IASMA ECO 2 berry is elliptic, and narrow (<13 mm) with the hilum barely visible. The flesh is soft, and the length of pedicel is short (<7 mm). In Teroldego and Lagrein the berry width is 13-18 mm, the hilum is visible, the pulp is firm, and the pedicel short.

The vesting period of IASMA ECO 2 is later than that of its parents.

DETAILED DESCRIPTION OF THE INVENTION

Figure 1:
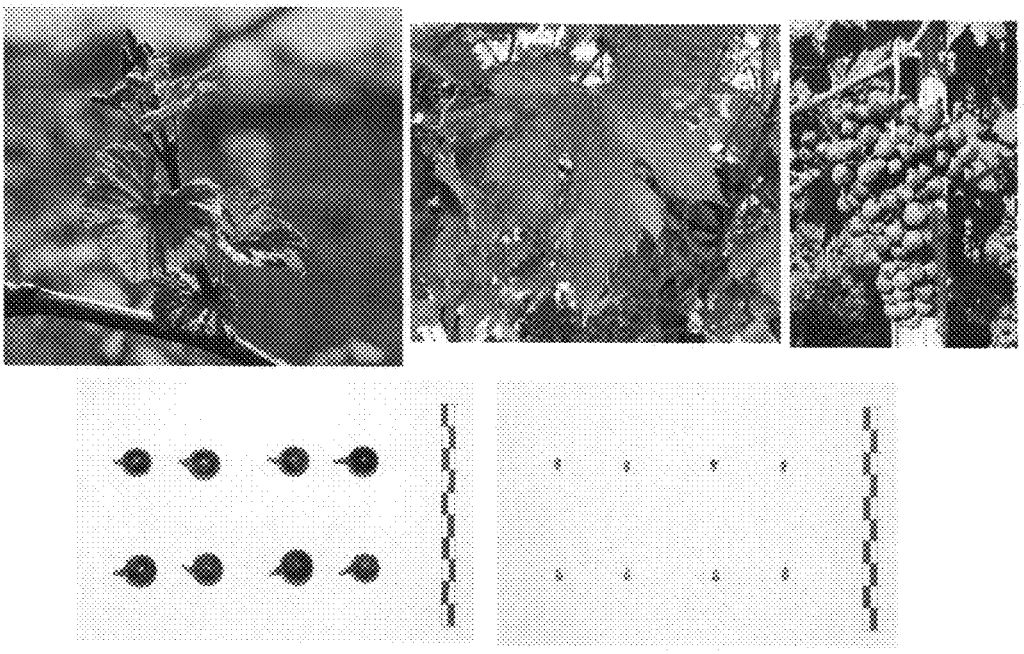
FIG. 1 provides photographic illustration in full color of "IASMA ECO 2" in various views. The colors are as nearly true as is reasonably possible in a color representation of this type.
Figure 2:
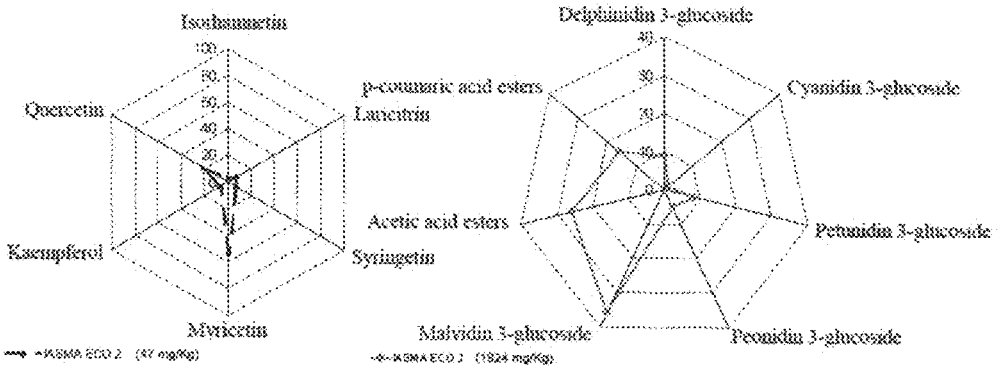
FIG. 2 provides a graphical representation of the average profile of aglycone flavonols and glycoside antocyanins in the present invention variety by percentile.
Figure 3:
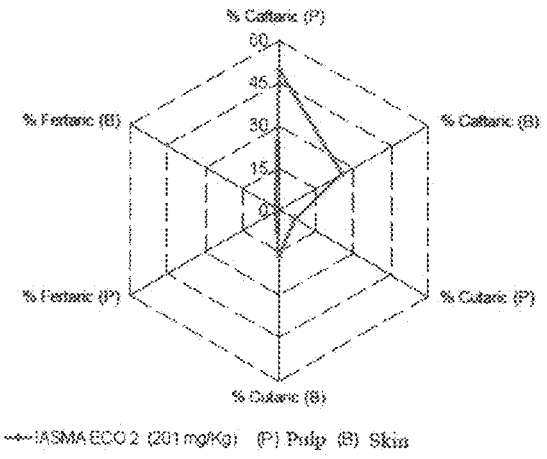
FIG. 3 provides a graphical representation of the average profile of cinnamic acids in the present invention variety by percentile and by mg/kg.
Figure 3:
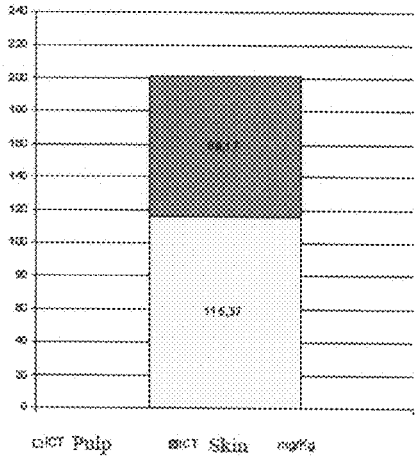

Throughout this specification, color names beginning with a small letter signify that the name of that color, as used in common speech, is aptly descriptive. Color names beginning with a capital letter or represented as a numerical designator indicate values based upon R.H.S. Colour Chart, published by The Royal Horticultural Society, London, England.

Throughout this specification subjective description values conform to those set forth by the Community Plant Variety Office (France) in the Technical Questionnaire for Grapevine varieties.

The descriptive matter which follows pertains to "IASMA ECO 2" plants grown in the vicinity of San Michele All'Adige (TN)—Trentino Alto Adige—Italy (46° 11' Lat. N, 11° 28' Long. E, 235 s.l.m.) from 2004 to 2010, and is believed to apply to plants of the variety grown under similar conditions of soil and climate elsewhere:

Young shoot: (10-30 cm).
- *Aperture of tip*.—(Fully open).
- *Distribution of anthocyanin pigmentation of tip*.—(Absent).
- *Intensity anthocyanin pigmentation of tip*.—(None).
- *Density prostrate hairs of tip*.—(None).
- *Density erect hairs of extremity*.—(None).

Shoot on blooming:
- *Attitude* 3.—(Semi-erect).
- *Color of dorsal side of internodes*.—(Green 150A-red 44B).
- *Color of ventral side of internodes*.—(Green 149).
- *Color of dorsal side of nodes*.—(Green 150A-red 44B).
- *Color of ventral side of nodes*.—(Green 149).
- *Density erect hairs on nodes*.—(None).
- *Density erect hairs on internodes*.—(None).
- *Density prostrate hairs on nodes*.—(None).
- *Density prostrate hairs on internodes*.—(None).
- *Anthocyanin pigmentation on the latent bud scales*.—(Basal).
- *Intensity anthocyanin pigmentation the bud scales*.—(Weak).

Tendrils:
- *Number of consecutive tendrils*.—(2 or less).
- *Length*.—(Short).

Young leaf:
- *Color of the upper side* 1.—(Green 136D).
- *Density prostrate hairs between the veins*.—(Medium).
- *Density erect hairs between the veins*.—(None).
- *Density prostrate hairs on veins*.—(Medium).
- *Density erect hairs on veins*.—(Medium).

Mature leaf:
- *Size of blade*.—(Medium).
- *Shape of blade*.—(Pentagonal).
- *Number of lobes*.—(Five).
- *Color of the upper side*.—(Medium green 149A).
- *Anthocyanin pigmentation veins on the upper side*.—(Absent).
- *Anthocyanin pigmentation veins on the lower side*.—(Absent).
- *Goffering of blade*.—(Weak).
- *Undulation of blade between main and lateral veins*.—(Present).
- *Profile in cross section*.—(Revolute).
- *Blistering of upper side*.—(Weak).
- *Shape of teeth*.—(Mixed).
- *Size of teeth in relation to blade size*.—(Small).
- *Length of teeth compared with their width*.—(Short).
- *Degree of opening of petiole sinus*.—(Very wide open).
- *Shape of base of petiole sinus*.—(Brace-shaped).
- *Teeth of the petiole sinus*.—(Absent).
- *Petiole sinus base delimited by veins*.—(Absent).
- *Degree of opening of upper lateral sinuses*.—(Slightly overlapped).
- *Shape of base of upper lateral sinuses*.—(U-shaped).
- *Teeth in the upper lateral sinuses*.—(Present).
- *Density of prostrate hairs between the veins of the lower side*.—(Medium).
- *Density of erect hairs between the veins of the lower side*.—(Absent).
- *Density of prostrate hairs on the veins of the side*.—(Low).
- *Density of erect hairs on the veins of the lower side*.—(Medium).
- *Prostrate hairs on the main veins of the upper side*.—(Absent).

*Erect hairs on the main veins of the upper side*.—(Absent).
*Density of prostrate hairs on petiole*.—(None).
*Density of erect hairs on petiole*.—(None).
*Length of petiole compared to middle vein*.—(Slightly longer).

Woody shoot:
*Cross section*.—(Elliptic).
*Structure of surface*.—(Striate).
*Main color*.—(Brownish).

Inflorescence:
*Sexual organs*.—(Stamens complete, gynoecium developed).

Bunch:
*Length*.—(Very long, >24 cm).
*Width*.—(Medium, <12 cm).
*Density*.—(Loose).
*Length of peduncle*.—(Short).
*Lignification of peduncle*.—(At the base only).
*Shape*.—(Conical).
*Number of wings*.—(1-2 wings).

Berry:
*Length*.—(Short, <13 mm).
*Width*.—(Narrow, <13 mm).
*Uniformity of size*.—(Uniform).
*Shape*.—(Globose).
*Color of the skin*.—(Blue black 89C).
*Uniformity of the color of the skin*.—(Uniform).
*Bloom*.—(Medium).
*Thickness of the skin*.—(Medium).
*Hilum*.—(Little visible).
*Intensity anthocyanin pigmentation of the flesh*.—(None).
*Juiciness of the flesh*.—(Very juicy).
*Must yield*.—(Medium).
*Firmness of the flesh*.—(Soft).
*Particular flavor*.—(None).
*Length of pedicel*.—(Short, <7 mm).
*Ease of detachment from pedicel*.—(Easy).
*Formation of seeds*.—(Complete).
*Time of autumn coloring of leaves*.—(Reddish).

Phenologic characteristics:
*Time of bud burst*.—Early.
*Time of full bloom*.—Medium.
*Time of berry ripening*.—Medium.
*Time of maturity*.—Medium-late.

Productive characteristics:
*Real fertility of the buds*.—1.44.
*Potential fertility*.—1.56.
*Position of the first bunch*.—3rd-4th bud.
*Production of grapes per vine*.—Kg 3.21.
*Yield per hectare quintal*.—115.
*Medium weight bunch*.—g 214.
*Medium weight berry*.—g 1.32.
*Sugars, brix degree*.—22.0.
*Total acid content*.—g/l 8.10.
*pH*.—3.25.

The present variety tested negative against each of the GFLV, ArMV, GLRaV-1, GLRaV-3, and GVA viruses.

FINDINGS OF MOLECULAR INVESTIGATIONS

DNA was extracted from young leaves of different accessions for each variety by using the Doyle and Doyle extraction method (1990) as modified by Grando et al. (2003). Molecular markers were obtained by analyzing DNA specimens at the 9 microsatellite loci specified by the European projects named Gen-Res81 and Grape-Gen06 for vine variety characterisation and at locus VMC1B11 (Vitis Microsatellite Consortium). In particular, the primers and amplification conditions described by Thomas and Scott (1993) for locus VVS2, Bowers et al. (1996) for loci VVMD5 and VVMD7, Bowers et al. (1999) for loci VVMD25, VVMD27, VVMD28 and VVMD32 and Sefc et al. (1999) for loci VrZAG62 and VrZAG79 were applied. PCR products were separated and analyzed with the Genetic Analyzer ABI3130 and the GeneMapper® v4.0 software.

| Microsatellite markers | | | | | | | | | | | | | | | | |
|---|---|---|---|---|---|---|---|---|---|---|---|---|---|---|---|---|
| IASMA ECO 2 | VVMD 5 | | | | VVMD 7 | | | | VVMD 25 | | | | VMD2 7 | | VVMD2 8 | |
| | 225 | 227 | | | 247 | 247 | | | 240 | 240 | | | 177 | 183 | 229 | 229 |
| IASMA ECO 2 | VVMD3 2 | | | | VVS2 | | | | VMC1B1 1 | | | | VrZAG6 2 | | VrZAG7 9 | |
| | 241 | 263 | | | 134 | 154 | | | 167 | 173 | | | 191 | 193 | 243 | 255 |

FINDINGS OF CULTIVATION TESTS

The series of summary tables below contain the findings for various vintage years concerning the present invention "IASMA ECO 2" vine variety compared to the reference vine variety.

Average data relative to some plant production parameters observed at the San Michele a/A (TN) vineyard (vintage years 2004-2010): vine grown following the Guyot method (arched shoot pruned at 8-10 sprouts/vine).

| | IASMA ECO 2 S. Michele a/A | TEROLDEGO S. Michele a/A |
|---|---|---|
| Grape/vine production (kg) | 3.17 | 4.12 |
| Actual shoot fertility | 1.44 | 1.29 |
| Potential shoot fertility | 1.56 | 1.57 |
| Wood/vine production (kg) | 0.559 | 0.494 |
| Must sugars (°Brix) | 22.00 | 20.80 |
| Moulds (%) bunch *botrytis* | 3.25 | 36.7 |
| Moulds (%) rachis desiccation | 0.00 | 0.00 |
| Grape/wood ratio | 5.68 | 8.340 |

Average data relative to mechanical bunch analysis and must chemical composition. Collection of bunches in the vintage years 2004-2010 at technological maturity (first or second half of September). Vineyard in S. Michele a./A. (S. Donà).

| IASMA ECO 2 | | | | |
|---|---|---|---|---|
| | | Values | | |
| | | | Limit v. | |
| | | Average v. | Min | max |
| Mechanical bunch analysis g | | | | |
| bunch average weight | | 214 | 106 | 237 |
| berry average weight | g | 1.30 | 1.12 | 1.70 |
| berry longitudinal diameter | mm | 13 | 10 | 15 |

-continued

| IASMA ECO 2 | | Values | | |
|---|---|---|---|---|
| | | | Limit v. | |
| | | Average v. | Min | max |
| berry average diameter | mm | 13 | 9 | 15 |
| Bunch composition | | | | |
| berries | (% in weight) | 94.5 | 93.3 | 96.7 |
| stems | (% in weight) | 5.5 | 3.3 | 6.7 |
| Berry composition | | | | |
| skins | (% in weight) | 21.6 | 15.9 | 30.8 |
| seeds | (% in weight) | 3.96 | 3.67 | 4.20 |
| pulp and must | (% in weight) | 68.5 | 57.9 | 74.0 |
| must yield | (% in volume/weight) | 62.3 | 52.8 | 66.1 |
| Chemical must composition | | | | |
| sugars | °Brix | 22.00 | 17.40 | 24.30 |
| total acidity | g/l | 8.10 | 6.91 | 10.50 |
| pH | | 3.25 | 3.13 | 3.41 |
| tartaric acid | g/l | 6.24 | 5.31 | 7.11 |
| malic acid | g/l | 3.94 | 1.65 | 6.22 |
| potassium | g/l | 1.33 | 0.89 | 1.94 |

Average data relative to the analysis of secondary metabolite profiles (aglycone flavonols and glycoside antocyanins of fruits) that characterise the variety's compositional phenotype.

Wine analysis.

Origin of grape: Vineyard in S. Michele a./A. (S. Donà) vintage years 2004-2010.

| IASMA ECO 2 | | Extreme values | |
|---|---|---|---|
| | Average | Min | Max |
| alcohol content % vol. | 12.54 | 11.92 | 13.28 |
| total acidity in tartaric acid g/l | 5.14 | 4.75 | 5.89 |
| dry extract g/l | 27.90 | 25.40 | 31.20 |
| pH | 3.62 | 3.40 | 3.85 |

-continued

| IASMA ECO 2 | | Extreme values | |
|---|---|---|---|
| | Average | Min | Max |
| total antocyanins (mg/l such as malvidin 3-monoglucoside chloride) | 967 | 823 | 1147 |
| total polyphenols mg/l (+) catechin | 2079 | 1653 | 2395 |

BEHAVIOUR IN VEGETATIVE MULTIPLICATION

Grafted vine affinity with the most popular holders—good

CULTIVATION CHARACTERISTICS AND SUITABILITY

The present invention vine variety shows medium vigour with early sprouting stage, with blue-black, medium-small, spherical berry with medium thickness skin. The bunch is medium-sized, winged, cylindrical and slightly straggly. It has a medium yield and is relatively resistant to *botrytis*. Its physiological maturity occurs in the third stage; it shows an excellent capacity to accumulate sugars while preserving medium-high acidity values. It can perfectly stand winter cold and shows a good resistance to downy mildew and powdery mildew. It prefers fertile hilly soils.

USE

The present invention vine variety is suited to produce both young and medium-long aged red wines. Young wines have a fruity taste (morello cherry and currant bush). When aged, spicy flavours become more accentuated; it shows a good acid resistance, also in case of small crops and particularly warm vintage years. The wines obtained from this vine variety show an excellent and deep ruby colour, good body, medium-high alcohol content, good tannin content, excellent texture and medium acidity. It is suitable to produce both young and medium-long aged wines; ageing and maturing create the typical character of noble red wines with spicy flavours and pleasant tannicity. It can also be successfully be used to cut other wines.

The invention claimed is:

1. A new and distinct variety of grapevine as herein illustrated and described.

* * * * *